United States Patent
Yee (10) Patent No.: US 11,583,231 B2
(45) Date of Patent: Feb. 21, 2023

(54) ADJUSTABLE ELECTRODE HEADSET

(71) Applicant: X Development LLC, Mountain View, CA (US)

(72) Inventor: Phillip Yee, San Francisco, CA (US)

(73) Assignee: X Development LLC, Mountain View, CA (US)

( * ) Notice: Subject to any disclaimer, the term of this patent is extended or adjusted under 35 U.S.C. 154(b) by 827 days.

(21) Appl. No.: 16/293,824

(22) Filed: Mar. 6, 2019

(65) Prior Publication Data
US 2020/0281530 A1     Sep. 10, 2020

(51) Int. Cl.
*A61B 5/05*    (2021.01)
*A61B 5/00*    (2006.01)
*A61B 5/291*   (2021.01)

(52) U.S. Cl.
CPC ............ *A61B 5/6843* (2013.01); *A61B 5/291* (2021.01); *A61B 5/6803* (2013.01); *A61B 2562/0209* (2013.01); *A61B 2562/222* (2013.01)

(58) Field of Classification Search
CPC ..... A61B 5/291; A61B 5/6814; A61B 5/6803; A61B 2562/164; A61B 5/282; A61B 5/6804; A61B 5/6831; A61B 5/0006; A61B 2018/00839; A61B 2560/0412; A41D 13/1281; A41D 1/002
USPC ....... 600/372, 382–384, 386, 388, 390, 393, 600/395, 544–545
See application file for complete search history.

(56) References Cited

U.S. PATENT DOCUMENTS

| | | | | |
|---|---|---|---|---|
| 3,998,213 A | * | 12/1976 | Price .................... | A61B 5/6814 600/383 |
| 4,928,696 A | * | 5/1990 | Henderson ............. | A61B 5/291 600/383 |
| 4,967,038 A | | 10/1990 | Gevins et al. | |

(Continued)

FOREIGN PATENT DOCUMENTS

| AU | 2011244986 | 11/2011 |
|---|---|---|
| AU | 2014240373 | 10/2014 |

(Continued)

OTHER PUBLICATIONS trans-cranial.com [online], "10/20 System Positioning Manual", Trans Cranial Technologies, Ldt, 2012, [retrieved on Jan. 23, 2019], retrieved from: URL<https://www.trans-cranial.com/docs/10_20_pos_man_vl_0_pdf.pdf> 20 pages.

*Primary Examiner* — Joseph A Stoklosa
*Assistant Examiner* — Brian M Antiskay
(74) *Attorney, Agent, or Firm* — Fish & Richardson P.C.

(57) ABSTRACT

An electroencephalography (EEG) headset can include an arrangement of straps that provides the ability to adjust the size and shape of the headset once disposed on a user's head. In some implementations, the headset can include a first elastic strap extending from a first side of the headset to a second side of the headset along a topside of the headset. The headset can also include a second strap including at least one inelastic portion and at least one elastic portion, at least one EEG electrode coupled to the second strap, a third elastic strap extending from the first side of the headset to the second side of the headset along an underside of the headset, and a plurality of connectors that couple the elastic first strap, the second strap, or the third elastic strap.

19 Claims, 10 Drawing Sheets

(56) References Cited

U.S. PATENT DOCUMENTS

| | | | |
|---|---|---|---|
| 5,293,867 A * | 3/1994 | Oommen | A61B 5/291 600/383 |
| 5,800,351 A * | 9/1998 | Mann | A61B 5/291 600/383 |
| 6,161,030 A * | 12/2000 | Levendowski | A61B 5/6804 600/383 |
| 7,551,952 B2 | 6/2009 | Gevins et al. | |
| 8,472,120 B2 | 6/2013 | Border et al. | |
| 8,477,425 B2 | 7/2013 | Border et al. | |
| 8,482,859 B2 | 7/2013 | Border et al. | |
| 8,488,246 B2 | 7/2013 | Border et al. | |
| 9,128,281 B2 | 9/2015 | Osterhout et al. | |
| 9,182,596 B2 | 11/2015 | Border et al. | |
| 9,229,227 B2 | 1/2016 | Border et al. | |
| 9,254,099 B2 | 2/2016 | Connor | |
| 9,341,843 B2 | 5/2016 | Border et al. | |
| 9,442,100 B2 | 9/2016 | Connor | |
| 9,451,899 B2 | 9/2016 | Ritchey et al. | |
| 9,529,385 B2 | 12/2016 | Connor | |
| 9,536,449 B2 | 1/2017 | Connor | |
| 9,675,292 B2 | 6/2017 | Fadem | |
| 9,907,473 B2 | 3/2018 | Tran | |
| 10,046,229 B2 | 8/2018 | Tran et al. | |
| 10,076,279 B2 | 9/2018 | Nahum | |
| 2005/0197756 A1 * | 9/2005 | Taylor | E02F 3/847 701/50 |
| 2007/0093706 A1 | 4/2007 | Gevins et al. | |
| 2007/0225585 A1 | 9/2007 | Washbon et al. | |
| 2009/0088619 A1 * | 4/2009 | Turner | A61B 5/291 600/383 |
| 2009/0105576 A1 | 4/2009 | Do et al. | |
| 2010/0036275 A1 * | 2/2010 | Alkire | A61B 5/0006 600/544 |
| 2010/0125190 A1 * | 5/2010 | Fadem | A61B 5/6814 600/383 |
| 2011/0098593 A1 * | 4/2011 | Low | A61B 5/0006 600/544 |
| 2011/0213664 A1 | 9/2011 | Osterhout et al. | |
| 2011/0214082 A1 | 9/2011 | Osterhout et al. | |
| 2012/0235884 A1 | 9/2012 | Miller et al. | |
| 2012/0235885 A1 | 9/2012 | Miller et al. | |
| 2012/0235887 A1 | 9/2012 | Border et al. | |
| 2012/0235900 A1 | 9/2012 | Border et al. | |
| 2012/0236030 A1 | 9/2012 | Border et al. | |
| 2012/0236031 A1 | 9/2012 | Haddick et al. | |
| 2012/0242678 A1 | 9/2012 | Border et al. | |
| 2012/0242698 A1 | 9/2012 | Haddick et al. | |
| 2012/0249797 A1 | 10/2012 | Haddick et al. | |
| 2014/0143064 A1 | 5/2014 | Tran | |
| 2015/0011857 A1 | 1/2015 | Henson et al. | |
| 2015/0112153 A1 | 4/2015 | Nahum | |
| 2015/0126873 A1 | 5/2015 | Connor | |
| 2015/0257674 A1 * | 9/2015 | Jordan | A61B 5/291 600/383 |
| 2015/0282760 A1 * | 10/2015 | Badower | A61B 5/6803 600/383 |
| 2016/0187654 A1 | 6/2016 | Border et al. | |
| 2016/0209648 A1 | 7/2016 | Haddick et al. | |
| 2016/0354005 A1 | 12/2016 | Oakley et al. | |
| 2017/0123495 A1 | 5/2017 | Leuthardt et al. | |
| 2017/0143228 A1 | 5/2017 | Leuthardt, Jr. et al. | |
| 2017/0173262 A1 | 6/2017 | Veltz | |
| 2017/0252534 A1 | 9/2017 | Nofzinger | |
| 2018/0239430 A1 | 8/2018 | Tadi et al. | |
| 2018/0271444 A1 * | 9/2018 | Floyd | A61B 5/4064 |
| 2018/0307314 A1 | 10/2018 | Connor | |
| 2019/0282168 A1 * | 9/2019 | Feiner | A61B 5/6835 |
| 2020/0245933 A1 | 8/2020 | Kentin et al. | |

FOREIGN PATENT DOCUMENTS

| | | |
|---|---|---|
| CA | 2963061 | 11/2015 |
| CN | 102460347 | 5/2012 |
| CN | 102906623 | 1/2013 |
| CN | 107106048 | 8/2017 |
| CN | 104768455 | 1/2018 |
| CN | 109804331 | 5/2019 |
| CN | 110234273 | 9/2019 |
| CN | 110558978 | 12/2019 |
| EP | 2698099 | 10/2018 |
| EP | 3592225 | 1/2020 |
| FR | 3028743 | 5/2016 |
| JP | 6332709 | 5/2018 |
| KR | 20170129689 | 11/2017 |
| RU | 31944 U1 | 9/2003 |
| RU | 2230483 | 6/2004 |
| RU | 2447871 | 4/2012 |
| TW | 201825045 | 11/2017 |
| WO | WO2008109694 | 9/2008 |
| WO | WO2008109699 | 9/2008 |
| WO | WO2012037290 | 3/2012 |
| WO | WO2012170816 | 12/2012 |
| WO | WO2014150199 | 9/2014 |
| WO | WO2007138598 | 6/2016 |
| WO | WO2017201088 | 11/2017 |
| WO | WO2018091823 | 5/2018 |
| WO | WO2018162482 | 9/2018 |
| WO | WO2019108968 | 6/2019 |

\* cited by examiner

PERSPECTIVE VIEW

FIG. 1A

RIGHT VIEW

FIG. 1B

LEFT VIEW

FIG. 1C

TOP VIEW

FIG. 1D

FRONT VIEW

FIG. 1E

BACK VIEW
FIG. 1F

LEFT VIEW
FIG. 1G

ADJUSTABLE ELECTRODE HEADSET

TECHNICAL FIELD

This specification generally describes technology related to electroencephalography (EEG), and more particularly, to technology related to headsets used to collect EEG measurements.

BACKGROUND

Electroencephalography is an electrophysiological monitoring method to record electrical activity of the brain. Electrical activity can be monitored using a headset that is positioned on a user's head so that electrodes are placed along the scalp. The electrodes measure voltage fluctuations resulting from ionic current within the neurons of the brain.

SUMMARY

Many EEG headsets apply pressure to the electrodes towards the scalp to reduce signal noise collected by electrodes. Due to the low measured voltages (e.g., 1 μV or 0.000001 V), the pressure is often needed to ensure constant and consistent signal detection. Many EEG headsets used for EEG measurements accomplish this using an elastic cap that stretches to form to the shape of the scalp when worn by a user. However, cap-based headsets can have limitations, such as high material manufacturing costs, and limited adaptability to accommodate to different head shapes and sizes. This is often due to caps having a prefixed size and shape, which results in the need to use multiple caps for different head sizes. Heads can also have different shapes, such as Western Head (narrower ear to ear), Eastern Head (wider ear to ear), top center peak, top flat, top centerline ridge, various curvature, which also makes it challenging to use cap-based EEG headsets to examine a large number of users.

The EEG headset disclosed herein addresses these and other limitations of many EEG headsets that are used for collecting EEG measurements. The headset includes an arrangement of straps that provides the ability to adjust the size and shape of the headset once disposed on a user's head. Inelastic straps are used to provide structure and support in regions of the user's head where electrodes are in contact with the scape, such as the forehead and the top of the user's head. Elastic straps are used to allow the headset shape to conform to the user's head shape and provide a tight fit. In some implementations, the headset can be configured in three different sizes, which allows it to accommodate roughly 95% of the human population.

The straps of the headset can be arranged and supported by one another to maintain constant loading, which is equalized among electrodes that contact the user's scalp. For example, three electrodes can be positioned along the top front-to-rear centerline of the head, and three electrodes horizontally arranged on the forehead, all of which were equalized with constant loads. In this example, force loading is not dependent on the elasticity of the elastic straps (which gain slack and stretch as it is worn), but force is achieved using the inelastic straps that can be adjusted and remain stable over longer periods. In some implementations, the adjustable headset can include a network of straps (e.g., a web-like structure of straps placed on the top of the user's head) that include attached sensors. The network of straps can provide the ability to position multiple electrodes in in different areas the user's scalp while providing similar advantages discussed above, such as adjustability to accommodate different head sizes and shapes.

In one general aspect, an EEG headset includes: a first elastic strap extending from a first side of the headset to a second side of the headset along a topside of the headset; a second strap comprising at least one inelastic portion and at least one elastic portion; at least one electroencephalogram (EEG) electrode coupled to the second strap; a third elastic strap extending from the first side of the headset to the second side of the headset along an underside of the headset; and a plurality of connectors that couple the elastic first strap, the second strap, or the third elastic strap.

One or more implementations can include the following optional features. For example, in some implementations, the plurality of connectors includes a first set of connectors that couples the second strap to the first elastic strap and a second set of connectors that couples the first elastic strap to the third elastic strap.

In some implementations, the at least one inelastic portion of the second strap includes: a front inelastic portion; and a rear inelastic portion joined to the front inelastic portion by the at least one elastic portion.

In some implementations, the at least one inelastic portion of the second strap comprises a topside inelastic portion. In such implementations, the at least one elastic portion of the second strap includes: a first elastic portion that joins the front inelastic portion to the topside inelastic portion, and a second elastic portion that joins the rear inelastic portion to the topside inelastic portion.

In some implementations, the at least one EEG electrode includes: three EEG electrodes that are coupled to the front inelastic portion of the second strap and configured to contact a forehead of a user's head when worn by the user; and a fourth electrode that is coupled to the topside inelastic portion of the second strap and configured to contact the top of the user's head when worn by the user.

In some implementations, the topside inelastic portion of the second strap is stitched to a portion of the first elastic strap.

In some implementations, the at least one EEG electrode is configured to contact a user's head when the headset is worn by a user; and the headset further comprises a plurality of wires for the at least one EEG electrode and configured to at least one of the first strap, the second strap, or the third strap.

In some implementations, the at least one inelastic portion of the second strap is stitched to the at least one elastic portion of the second strap.

In some implementations, the first strap, the second strap, and the third strap are ring straps; and the plurality of connectors are ring connectors.

In some implementations, an arrangement of the first, second, and third straps is configured to evenly distribute pressure among the at least one EEG electrode.

In another general aspect, an EEG headset includes a central pressure distribution strap. The central pressure distribution strap includes a front inelastic portion comprising, and a posterior inelastic portion joined to the front inelastic portion by at least one elastic portion. The headset also includes at least one EEG electrode coupled to the central pressure distribution strap.

In some implementations, the central pressure distribution strap includes a topside inelastic portion. In such implementations, at least one elastic portion of the central pressure distribution strap includes: a first elastic portion that joins the front inelastic portion to the topside inelastic portion, and a second elastic portion that joins the posterior inelastic portion to the topside inelastic portion.

In some implementations, the headset also includes: at least one elastic strap. In such implementations, the topside inelastic portion of the central pressure distribution strap is stitched to an elastic strap from among the at least one elastic strap.

In some implementations, the at least one EEG electrode includes three EEG electrodes that are coupled to the front inelastic portion of the central pressure distribution strap and configured to contact a forehead of a user's head when worn by a user. In such implementations, the headset includes a fourth electrode that is coupled to the topside inelastic portion of the central pressure distribution strap and configured to contact a top of the user's head when worn by the user.

In some implementations, the at least one EEG electrode is configured to contact a user's head when the headset is worn by a user. In such implementations, the headset further includes a plurality of wires for the at least one EEG electrode and configured to the central pressure distribution strap.

In yet another general aspect, an EEG headset includes a central strap configured to be placed over a crown of a head when worn. The central strap includes front and back inelastic portions joined by at least one elastic portion. The headset also includes at least one EEG electrode coupled to the central strap; a chin strap extending from a first side of the headset to a second side of the headset; and a top elastic strap extending across the central strap from the first side of the headset to the second side of the headset. The top elastic strap is coupled to the central strap and to the chin strap by a plurality of connectors.

In some implementations, the central strap includes a topside inelastic portion. In such implementations, the at least one elastic portion of the central strap includes: a first elastic portion that joins the front inelastic portion to the topside inelastic portion, and a second elastic portion that joins the back inelastic portion to the topside inelastic portion.

In some implementations, the at least one EEG electrode includes three EEG electrodes that are coupled to the front inelastic portion of the second strap and configured to contact a forehead of a user's head when worn by a user. The at least one EEG electrode also includes a fourth electrode that is coupled to the topside inelastic portion of the second strap and configured to contact the top of the user's head when worn by the user.

In some implementations, the topside inelastic portion of the central strap is stitched to a portion of the top elastic strap.

In some implementations, the central strap, the chin strap, and the top elastic strap are ring straps and the plurality of connectors are ring connectors.

The details of one or more implementations are set forth in the accompanying drawings and the description below. Other potential features and advantages will become apparent from the description, the drawings, and the claims.

BRIEF DESCRIPTION OF THE DRAWINGS

In the drawings, like reference numbers represent corresponding parts throughout.

DETAILED DESCRIPTION

Figure 1A:
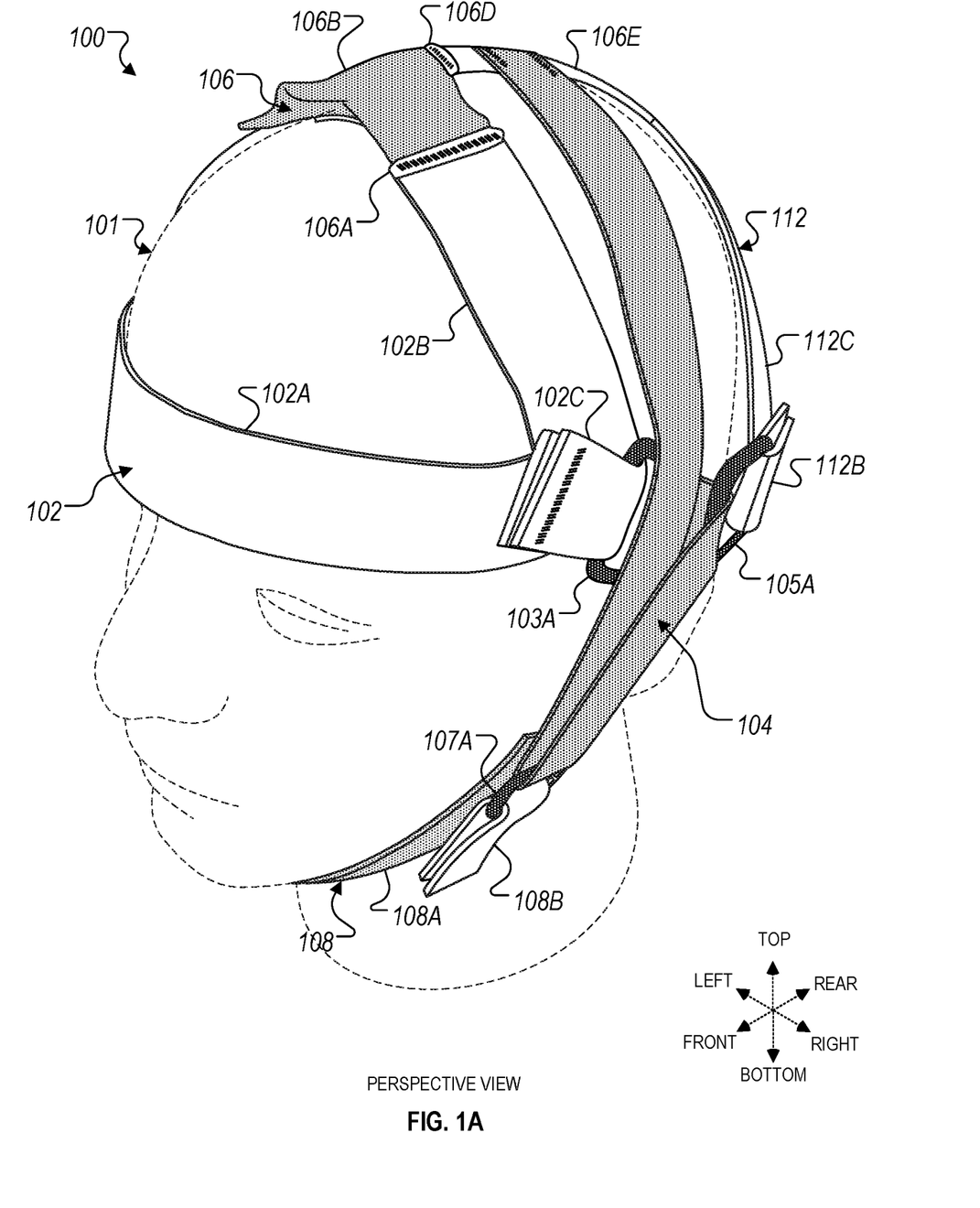
FIG. 1A depicts a perspective view of an example of an adjustable headset.

FIGS. 1A-1F depict different views of an adjustable EEG headset 100 to be disposed on a user's head 101 in association with the collection of EEG measurements. Referring initially to FIG. 1A, a perspective view of the headset 100 is depicted. The head set 110 includes straps 102, 104, 106, 108, and 112, which are affixed or otherwise coupled to one another to form the structure of the headset 100. Each strap of the headset 100 includes different portions to be disposed on a different part of a user's head 101, which are depicted in more detail in FIGS. 1B-1F.

Referring briefly to the straps of the headset 100, straps 102 and 112 can be inelastic straps of fixed length that are used for maintain a structure of the headset 100 when positioned on the user's head 101. For example, portions of the strap 102 are positioned nearby the user's forehead (as shown in FIG. 1E) whereas portions of the strap 112 are positioned nearby the rear crown of the user's head 101 (as shown in FIG. 1F). Strap 104 can be an elastic strap that made from is stretchable material to accommodate different head sizes and shapes. Strap 106 can be a pressure distribution strap to be disposed on the top of the user's head 101 to stabilize the headset 100 atop the user's head 101. Strap 108 can be a chin strap that to be placed underneath a chin of the user's head 101 to stabilize the bottom of the headset 100 beneath the user's head 101.

Figure 1B:
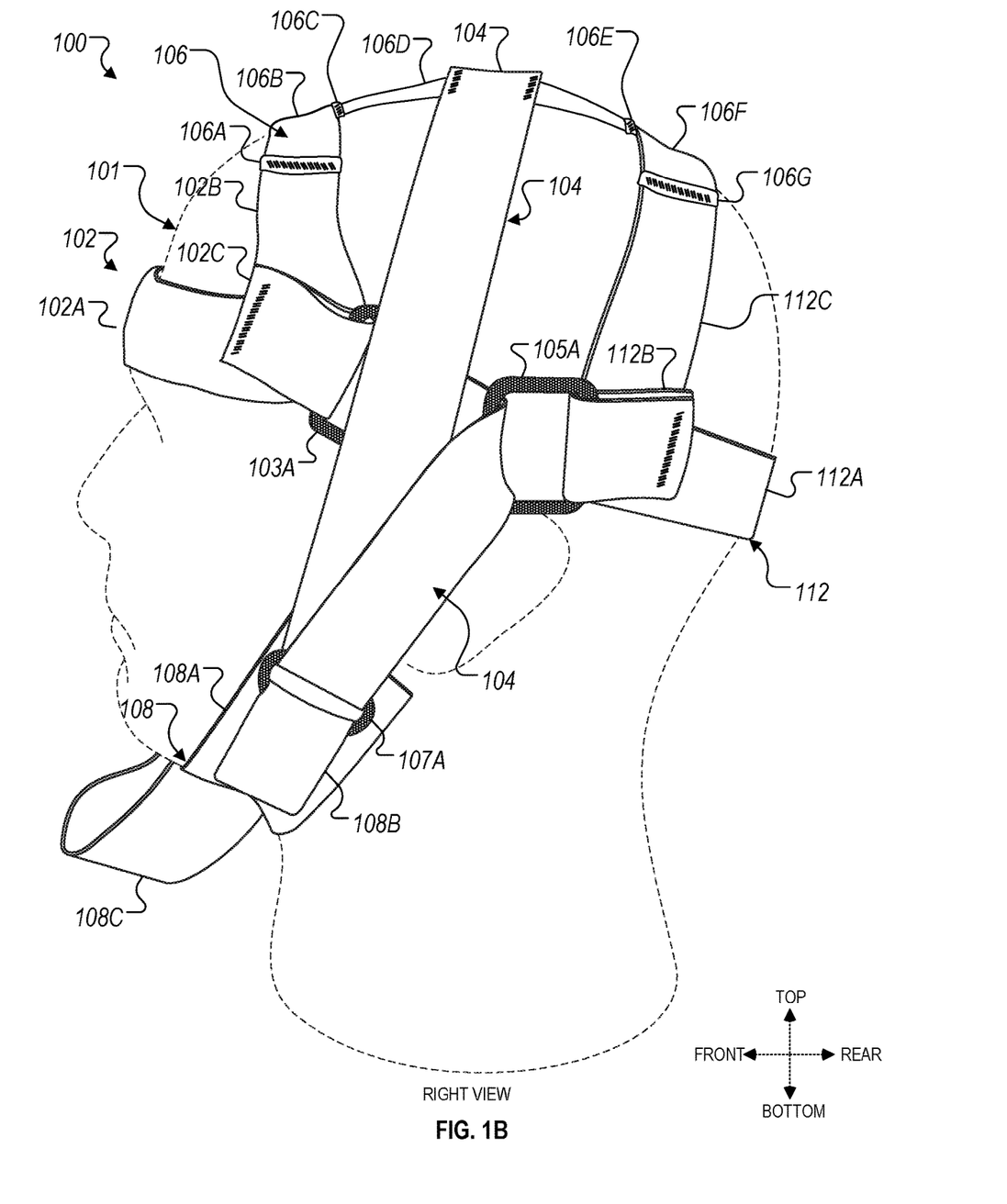
FIG. 1B depicts a left side view of the adjustable EEG headset depicted in FIG. 1A.
Figure 1C:
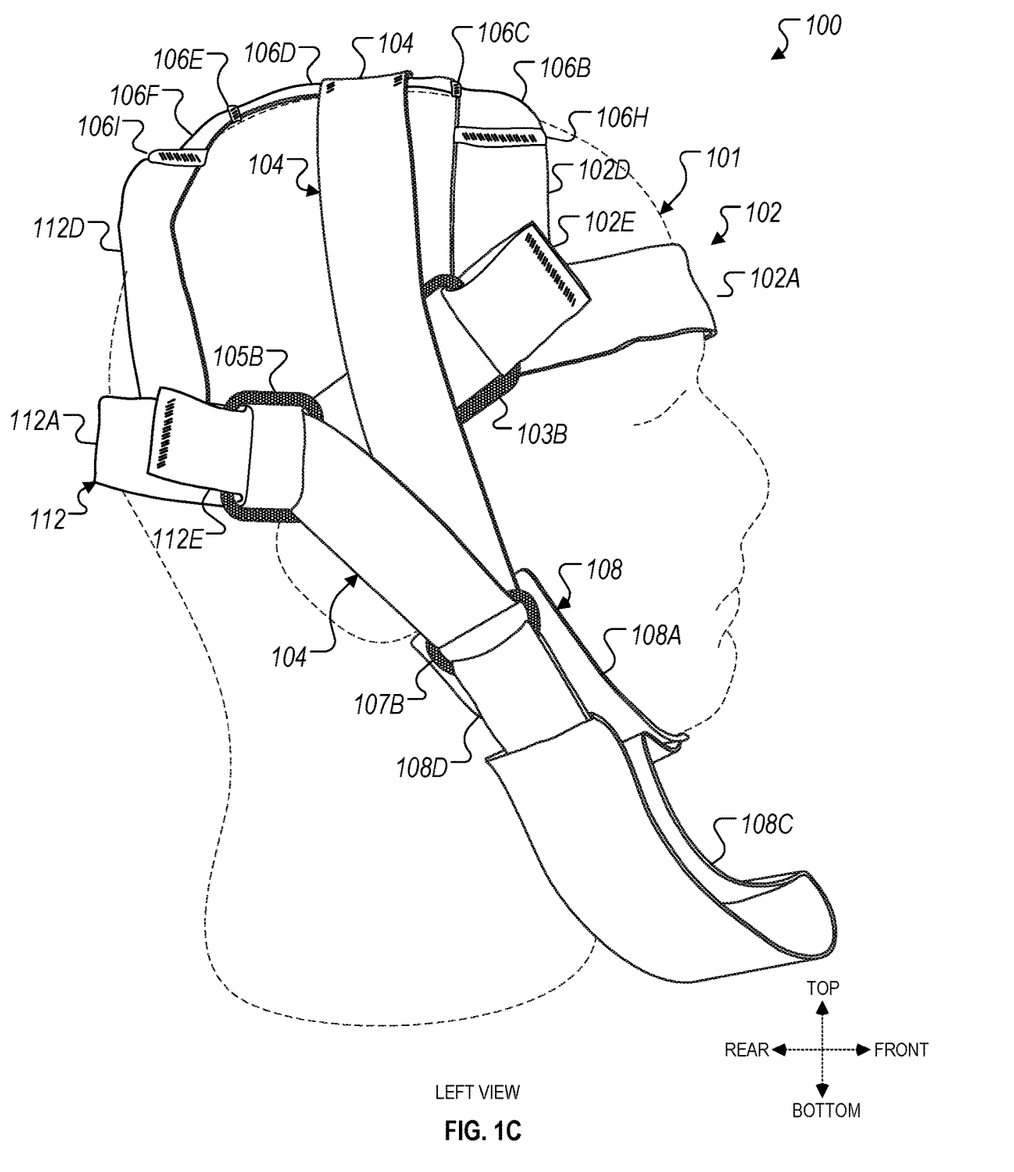
FIG. 1C depicts a right side view of the adjustable EEG headset depicted in FIG. 1A.

In more detail, referring to FIGS. 1B and 1C, the strap 102 includes a front portion 102A (shown in FIGS. 1B and 1C) to be disposed nearby the user's forehead, a side portion 102B (shown in FIG. 1B) to be disposed on the front-right portion of the user's head 101, and a side portion 102D (shown in FIG. 1C) to be disposed on the front-left portion of the user's head 101. The strap 102 also includes an attachment portion 102C (shown in FIG. 1B) that couples the front portion 102A to the side portion 102B along the front-right side of the headset 100 (when assembled), and an attachment portion 102E (shown in FIG. 1C) that couples the front portion 102A to the side portion 102D along the front-left portion of the headset 100 (when assembled).

Still referring to FIGS. 1B and 1C, the strap 112 includes a back portion 112A (shown in FIGS. 1B and 1C) to be disposed on or near the crown of the user's head 101, a side portion 112B (shown in FIG. 1B) to be disposed on the rear-right portion of the user's head 101, and a side portion 112D (shown in FIG. 1C) to be disposed on a rear-left portion of the user's head 101. The strap 112 also includes an attachment portion 112B (shown in FIG. 1B) that couples the back portion 112A to the side portion 112C along the rear-right side of the headset 100 (when assembled), and an attachment portion 112E (shown in FIG. 1C) that couples the back portion 112A to the side portion 112D along the rear-left portion of the headset 100 (when assembled).

Still referring to FIGS. 1B and 1C, the strap 104 extends from one side of the headset 100 to the other side of the headset 100 along the top of the headset 100 (as shown in FIGS. 1A, 1B and 1C). When the headset 100 is assembled, the right side of the strap 104 (shown in FIG. 1B) is coupled to the attachment portion 102C through a connector 103A, the attachment portion 112B through a connector 105A, and the attachment portion 108B through a connector 107A, along the left side of the headset 100. Also, when the headset 100 is assembled, the left side of the strap 104 (shown in FIG. 1C) is coupled to the attachment portion 102E through a connector 103B, the attachment portion 112E through a connector 105B, and the attachment portion 108D through a connector 107B, along the left side of the headset 100.

Figure 1D:
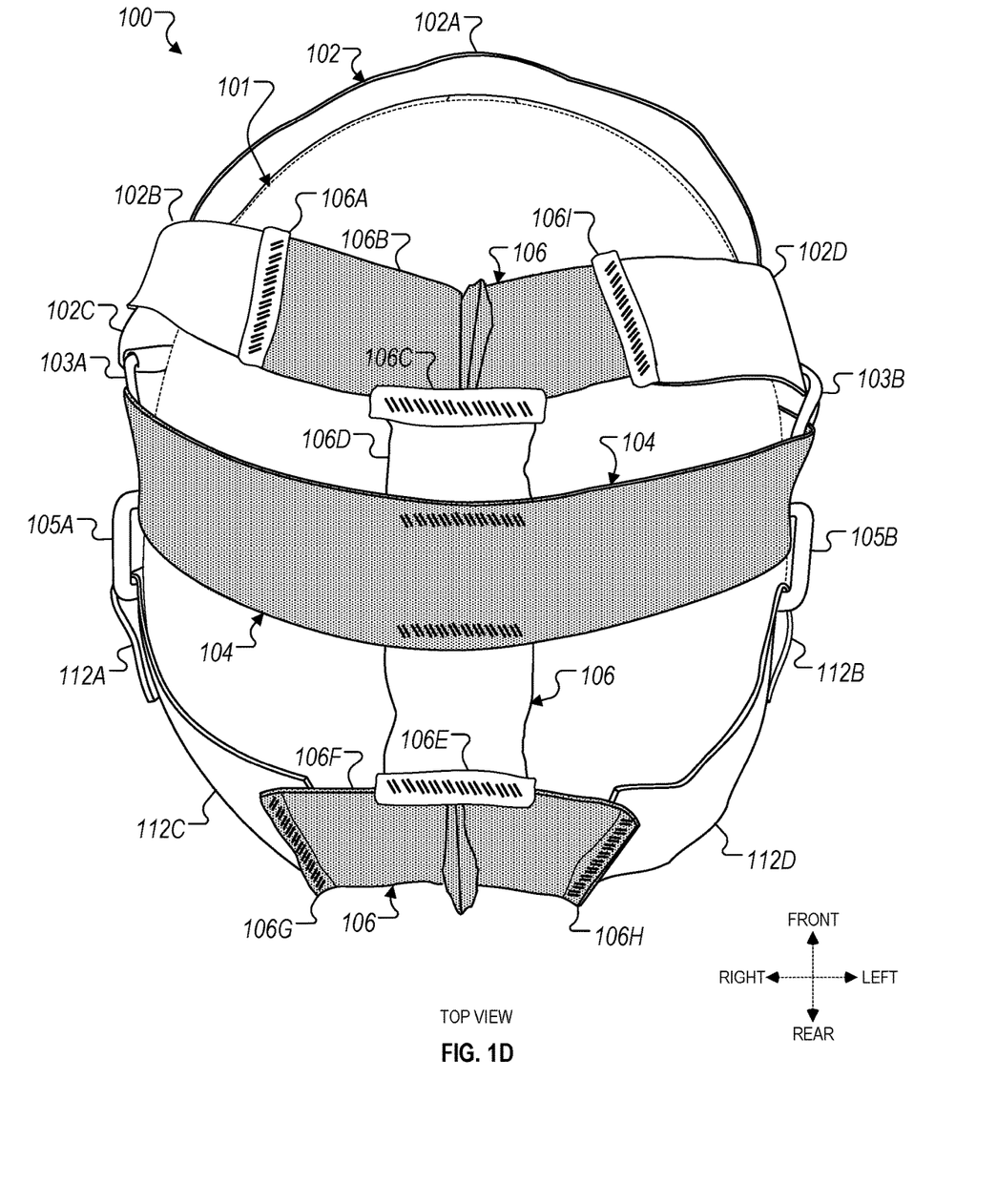
FIG. 1D depicts a top view of the adjustable EEG headset depicted in FIG. 1A.
Figure 1E:
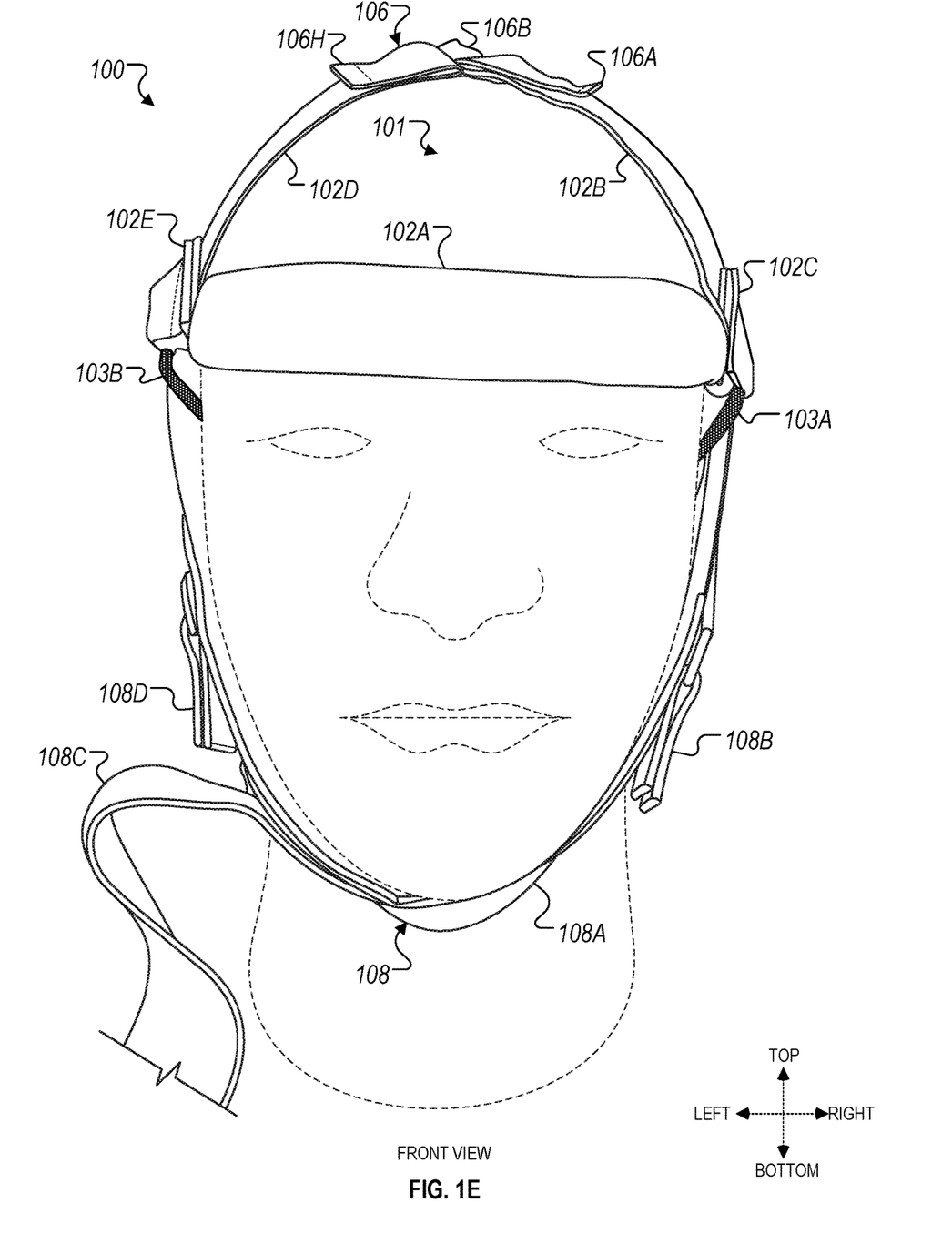
FIG. 1E depicts a front view of the adjustable EEG headset depicted in FIG. 1A.
Figure 1F:
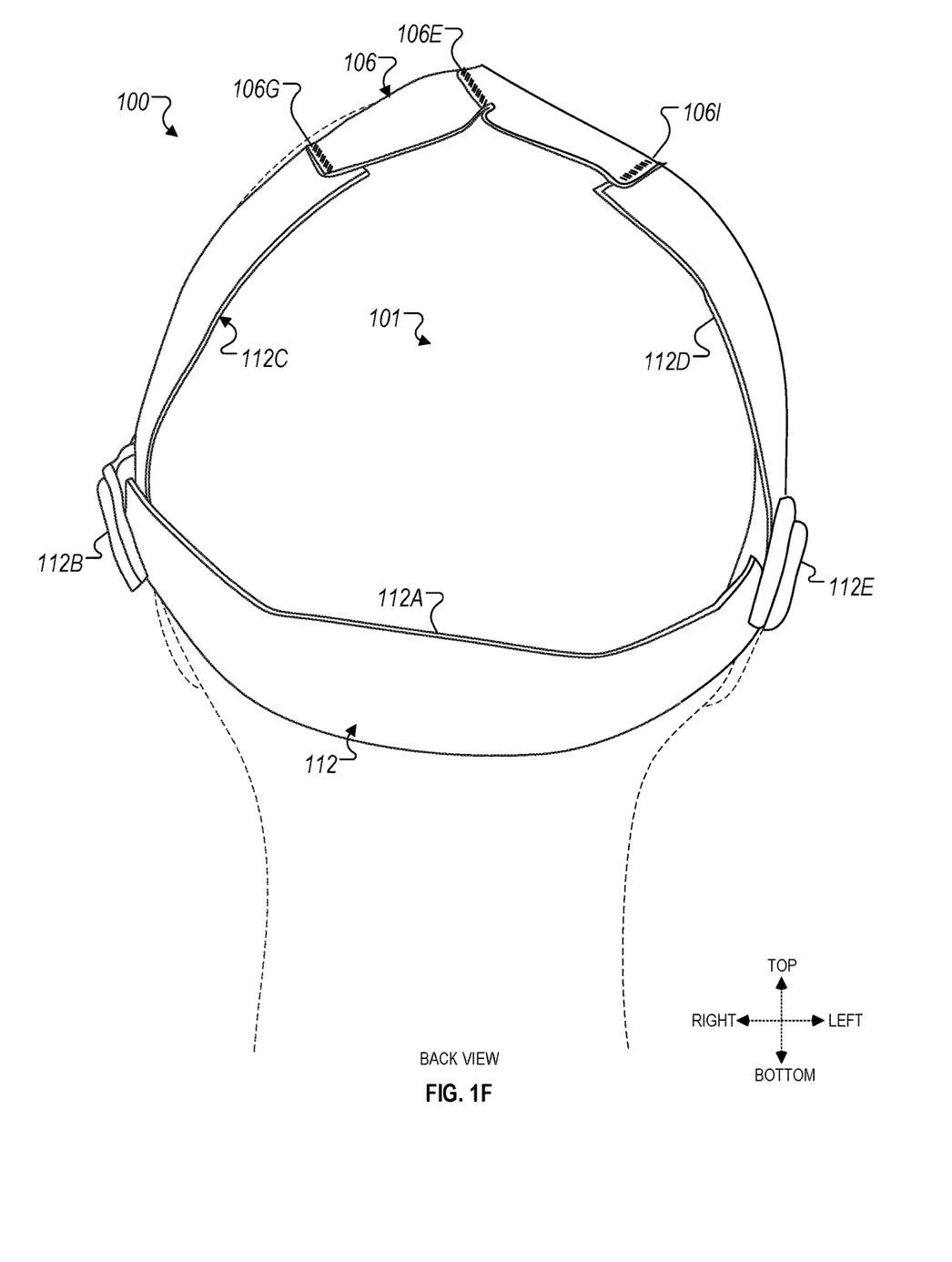
FIG. 1F depicts a back view of the adjustable EEG headset depicted in FIG. 1A.

Referring now to FIG. 1D, the strap 106 can be a pressure distribution strap or a central strap that is to be disposed on top of the user's head 101 when the headset 100 is worn by a user. The strap 106 includes elastic portions 106B and 106F that are capable of stretching along the top-front and top-rear portions of the headset 100, respectively, to accommodate various head sizes and head shapes. For example, if the headset 100 is placed on a larger head, the elasticity of the portions 106B and 106F allows the headset 100 to stretch alongside the top so that the headset 100 can be comfortably worn by the user. The strap 106 also includes an inelastic portion 106D that is used to stabilize the positioning of the headset 100 along the top of the user's head 101.

Referring still to FIG. 1D, when the headset 100 is assembled, the side portion 102B of the strap 102 is coupled to the right side of the elastic portion 106B of the strap 106 by an attachment portion 106A along the front-right side of the headset 100. The side portion 102D of the strap 102 is coupled to the left side of the elastic portion 106B of the strap 106 by an attachment portion 106I along the front-left side of the headset 100. Also, when the headset 100 is assembled, the side portion 112C of the strap 112 is coupled to the right side of the elastic portion 106F of the strap 106 by an attachment portion 106G along the back-right side of the headset 100. The side portion 112D of the strap 112 is coupled to the left side of the elastic portion 106F of the strap 106 by an attachment portion 106H along the back-left side of the headset 100.

Referring back to FIGS. 1B and 1C, the strap 108 includes a chin portion 108A (shown in FIG. 1B) to be placed underneath a chin of the user's head 101 when the headset is worn by the user 101. The strap 108 includes an attachment portion 108B (shown in FIG. 1B) that is coupled to the strap 104 along the right side of the headset 100 by a connector 107A. The strap 108 also includes an attachment portion 108D (shown in FIG. 1C) that is coupled to the strap 104 along the left side of the headset 100 by a connector 107B. The strap 108 also includes an extension portion 108C (shown in FIGS. 1B, 1C, and 1E) to adjust the horizontal length of the strap 108 along the bottom of the headset 100. The adjustable horizontal length of the strap 108 permits the headset 100 to be worn by user's that have different chin sizes and shapes.

As shown in FIGS. 1E and 1F, when the headset 100 is worn by a user, various portions of its straps can be adjusted to accommodate the size and shape of the user's head. For example, as discussed above, the elastic portions of the strap 106 (e.g., the portions 106B and 106F shown in FIG. 1D) can be stretched to accommodate different head shapes and sizes while providing a comfortable fit. Additionally, the elasticity of the chin portion 108A and the adjustable horizonal length of the strap 108 using the adjustment portion 108C allows the headset 100 to accommodate different chin shapes and sizes. The strap 104 reinforces the positioning of the headset 100 when worn by extending from a first side of the user's head 101 to the opposite side of the user's head 101 along the top of the user's head 101. The elastic portions of the headset 100 provide adjustability by allowing specific regions of the headset to stretch.

Additionally, the headset 100 includes inelastic portions that provide stability and consistent contact with areas of the user's head 101. For example, electrodes can be attached to the inelastic portions. This stability of the inelastic portions may aid in maintaining consistent contact between the electrodes and the user's head, as discussed in detail below in reference to FIG. 3. For example, the front portion 102A of the strap 102 is disposed over or nearby a forehead of the user's head 101 (shown in FIG. 1F), whereas the back portion 112A of the strap 112 is disposed over or nearby a crown of the user's head 101 (shown in FIG. 1F). These portions of the headset 100 are inelastic as they can be used to attach electrodes that are used for collecting EEG measurements. Moreover, due to their inelastic nature, these portions provide structure support to prevent unnecessary movement during the data collection process.

As shown in FIGS. 1A-1E, components of the headset 100 can either be permanently attached to one another (e.g., through stitching), or removably attached to one another (e.g., through the use of connectors). For example, in some implementations, the strap 102 is formed by stitching the right side of the front portion 102A and the side portion 102B nearby the attachment portion 102C (as shown in FIG. 1B) and stitching the left side of the front portion 102A to the side portion 102E nearby the attachment portion 102E (as shown in FIG. 1C). In other implementations, the attachment portions 102C and 102E can use other suitable attachment techniques to form the strap 102, such as button-hold attachment, hook and loop fastener-based-based attachment, or zipper-based attachment. In this respect, the attachment portions 102C, 102E, 112B, and 112E can employ various types of attachment mechanisms to form the straps 102 and 112, respectively.

Additionally, as shown in FIGS. 1A-1E, the connectors 103A, 103B, 105A, 105B, 107A, and 107B can be ring connectors that used to fold portions of the straps for assembling the headset 100. For instance, in the example shown in FIG. 1B, the top portion of the strap 104 extends downward from the top of the headset 100 to the bottom of the headset, folds around the connector 107A, then extends upward toward the top of the headset 100, folds over the connector 105A, and then is wrapped around a side of the connector 103A. In this example, the connectors 103A, 105A, and 107A are used couple the strap 104 to the strap 102 (e.g., using the connector 103A), the strap 112 (e.g., using the connector 105A), and the strap 107A (e.g., using the connector 107A). The ring connectors permit the strap 104 to be able to stretch along the side of the headset 100 to help with positioning and comfort when the headset 100 is worn by a user.

In some implementations, the connectors 103A, 103B, 105A, 105B, 107A, and 107B can be configured to use other types of attachment techniques to couple the straps 102, 104, 108, and 112 to one another. For example, the connectors can include buckles and receivers that are attached to one another to allow a portion of the strap 104 to be connected to corresponding portions of the straps 102, 108, and 112 as shown in FIG. 1B. As another example, the connectors can include other types of physical attachment mechanisms, such as button-hold attachment, hook and loop-based attachment, or zipper-based attachment, as discussed above for the attachment modules 102C, 102E, 112B, and 112E.

Figure 1G:
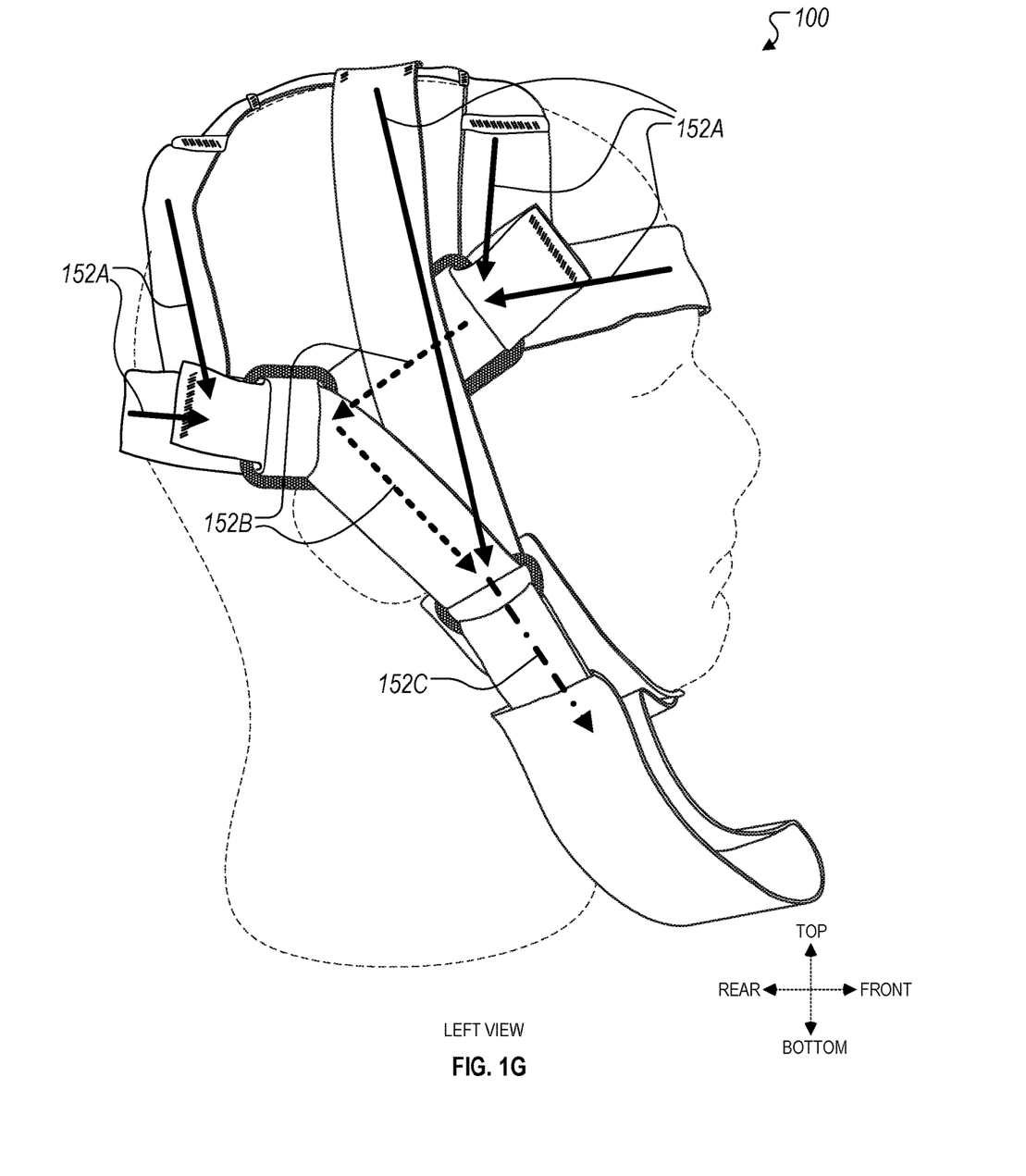
FIG. 1G depicts force loading along the left side of the adjustable EEG headset depicted in FIG. 1A.

Referring now to FIG. 1G, force loading along the left side of the adjustable EEG headset is depicted. The arrangement and configuration of the straps in the assembled headset 100, as discussed above, can be used to improve mechanical loading and adjustment when worn by a user. As shown in FIG. 1G, primary forces 152A from direct mechanical loading can occur on along the strap 104, the front portion 102A, the side portion 102B, the back portion 112A, and the side portion 112D. Resultant secondary forces 152B can be provided by combining the primary forces 152A provided along the front portion 102A and the side portion 102B, as well as the back portion 112A and the side portion 112D, respectively. The secondary forces 152B are along the strap 104 in a direction from connector 103B to the connector 105B, and also along the strap 104 in the direction from the connector 105B to the connector 107B. A resultant force 152C is then provided along the strap 108 toward the user's chin by combing the primary downward force 152A along the strap 104 and the secondary force 152B provided along the strap 104 from the connector 105B and the connector 107B. This enables even loading along all areas of the headset, which is useful in implementations where the headset 100 included attached electrodes, and enables even loading on all electrodes with a single adjustment of the strap 108.

Figure 2A:
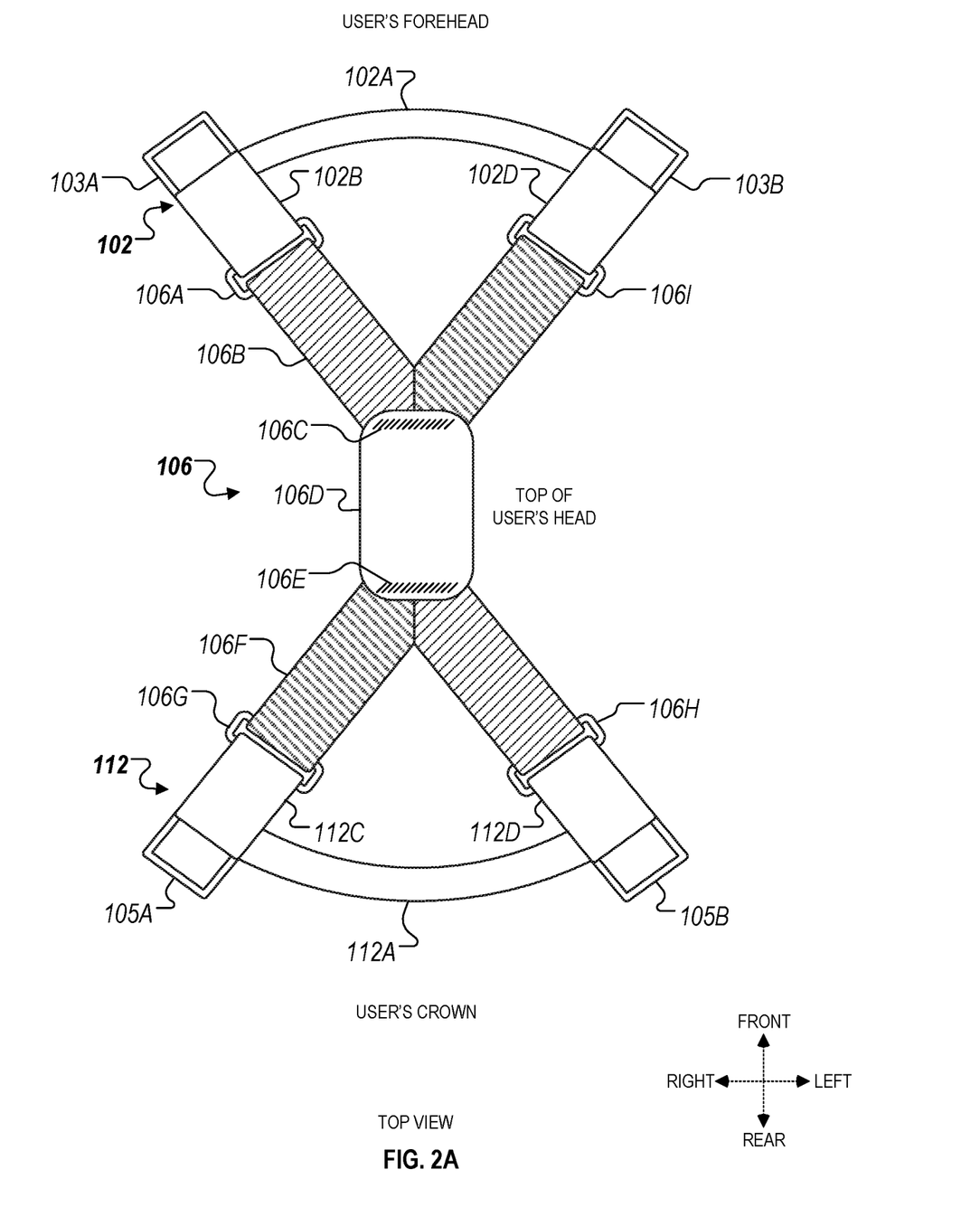
FIG. 2A is a conceptual representation of a top of an implementation of an adjustable EEG headset with single inelastic top portion.

Referring now to FIG. 2A, a conceptual representation of a top of the headset 100 is shown for simplicity. The strap 102 is to be disposed on or nearby the forehead of a user's head and includes a front portion 102A, and side portions 102B and 102D, as discussed above. The strap 112 is to be disposed on or nearby the crown of the user's head and includes a back portion 112A and side portions 112C and 112D. The strap 106 includes elastic portions 106B and 106F that are coupled to the straps 102 and 112, respectively, and an inelastic portion 106D to be disposed on top of the user's head. As discussed above, the elastic portions 106B and 106F permit the top of the headset 100 to be stretchable along the front and rear so that the headset 100 can be used to accommodate different head shapes and sizes. The inelastic portion 106D provides stability over the top of the user's head, and in some instances, can have attached electrodes to collect EEG measurements.

As discussed above, the headset 100 includes various attachment portions that provide interfaces between various components of the headset 100. For instance, the attachment portion 106A couples the side portion 102B of the strap 102 to the elastic portion 106B of the strap 106 and the attachment portion 106I couples the side portion 102D of the strap 102 to the elastic portion 106B of the strap 106. The attachment portion 106G couples the side portion 112C of the strap 112 to the elastic portion 106F of the strap 106 and the attachment portion 106H couples the side portion 112D of the strap 112 to the elastic portion 106F of the strap 106. Additionally, attachment portions 106C and 106E allow the elastic portions 106B and 106F to be coupled to the inelastic portion 106D of the strap 106.

As discussed above, and shown in the implementations depicted in FIGS. 1A-1E, the attachment portions include stitching that connects two components together. For example, the top of the inelastic portion 106D can be stitched to the elastic portion 106C to represent the attachment portion 106C. However, in other implementations, the attachment portions can provide other types of removable or permanent attachment devices that does not involve stitching. For example, in the implementation depicted in FIG. 2, the attachment modules 106A, 106G, 106H, and 106I are ring connectors that couple portions of the straps 102 and 112 to the corresponding portions of the strap 106. In other examples, other suitable attachment techniques may also be used.

Figure 2B:
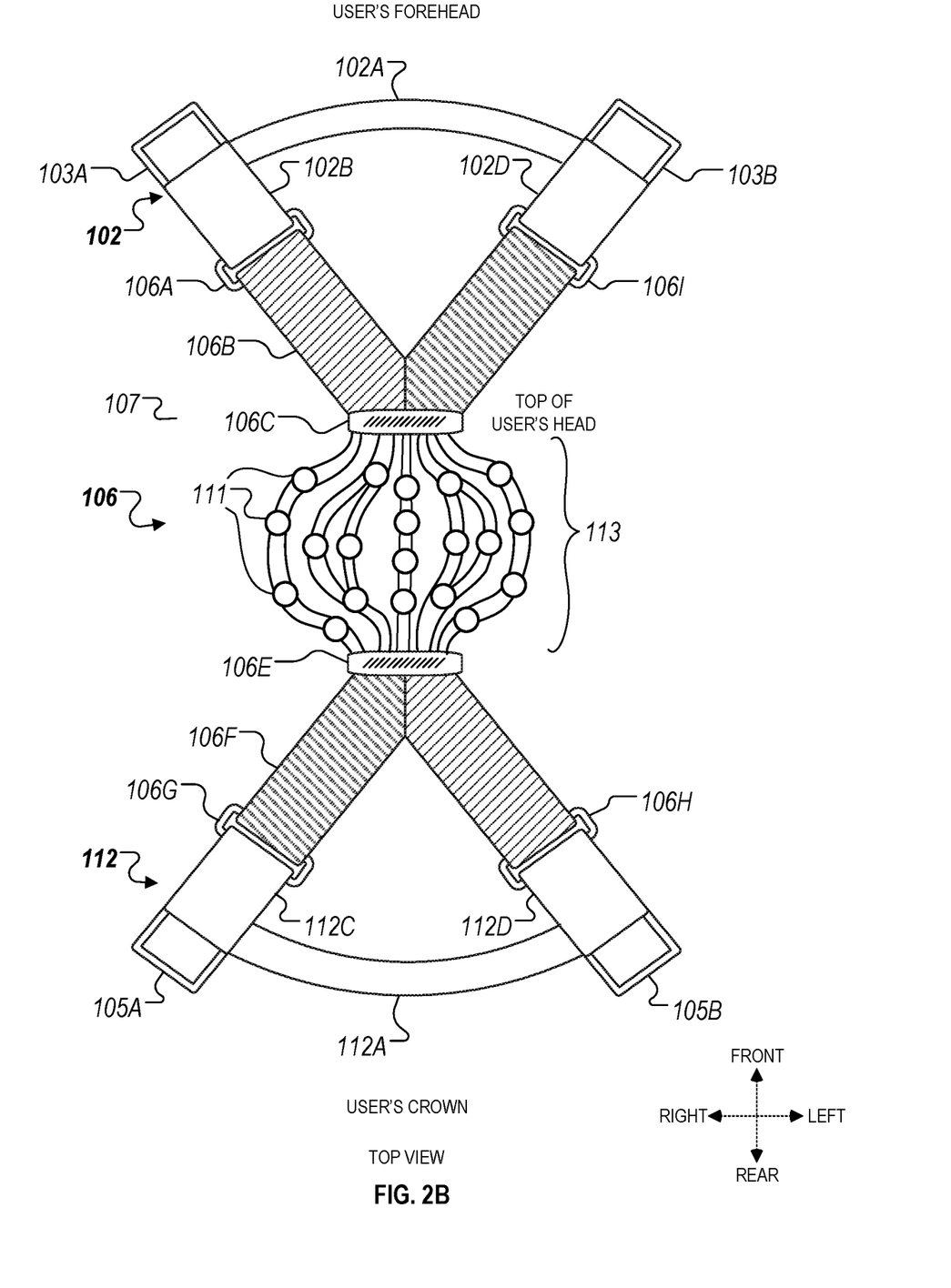
FIG. 2B is a conceptual representation of a top of one implementation of an adjustable EEG headset with a webbed inelastic portion.

Referring now to FIG. 2B, a conceptual representation of a top of an alternative implementation of an adjustable EEG headset is shown. In this example, the strap 106 includes a webbed portion 113 that includes an arrangement of inelastic straps with attached electrodes 111. The arrangement of the webbed portion 113 allows electrodes to be positioned on specified areas of the top of the user's head for the collection of EEG signals from the corresponding areas. The electrodes 111 can be attached to the inelastic straps using any suitable means of attachment. In different implementations, the pattern employed in webbed portion 113 can be adjusted to generate a desired electrode placement pattern. For example, the number straps in the webbed portion 113 can be increased to increase the number of electrodes to be disposed on top of the user's head. As another example, the number of branches within the webbed pattern can be adjusted to increase or decrease the distance between electrodes when disposed on the user's head. In some implementations, the webbed portion 113 is detachable from the attachment portions 106C and 106E to allow for multiple different webbed portions to be used with the same headset (e.g., for different types of EEG collection procedures). In such implementations, multiple different webbed portions 113 having different sensor placement patterns can be used with the same set of straps of the headset without requiring the use of multiple headsets.

Figure 3:
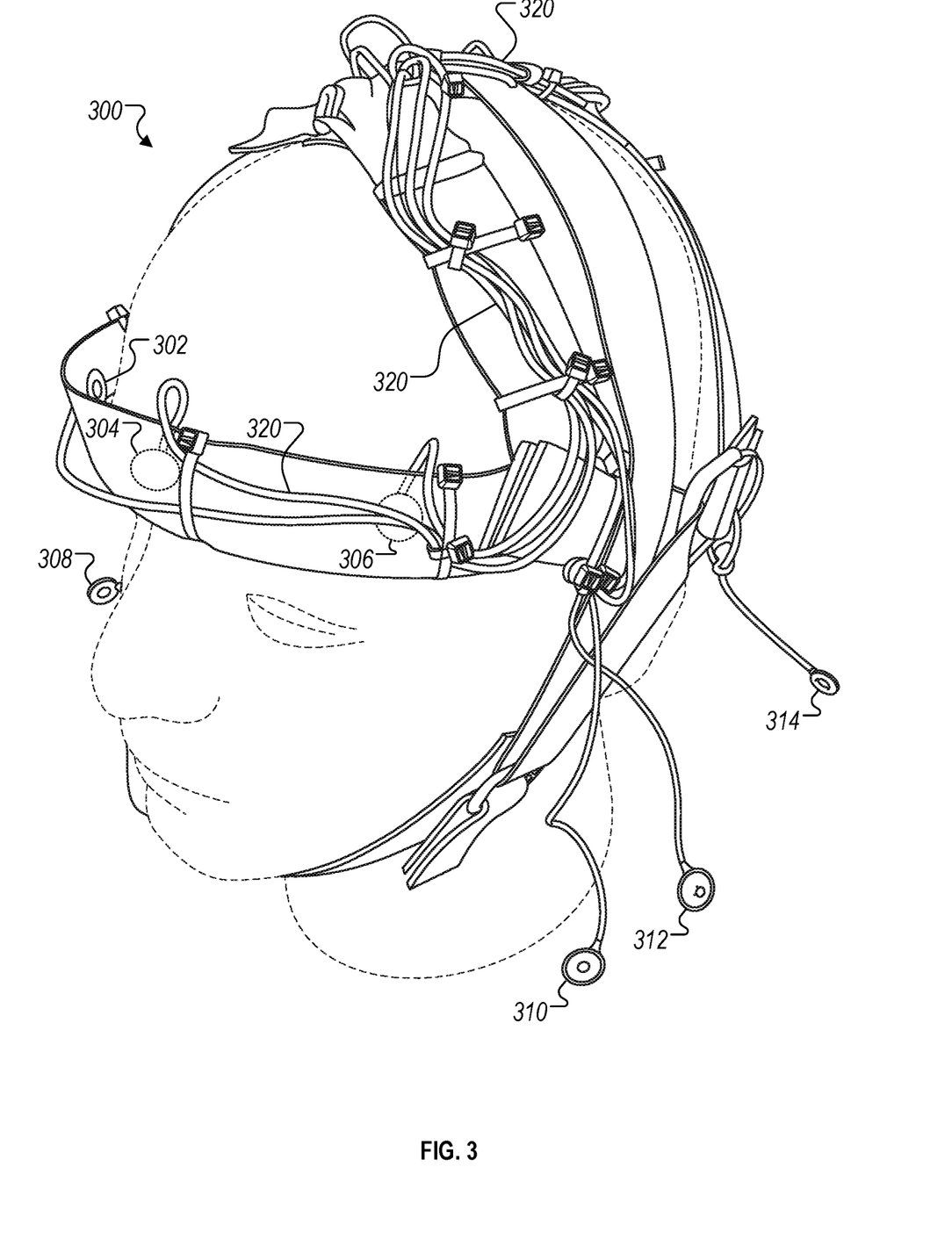
FIG. 3 depicts a perspective view of an example of an adjustable EEG headset with attached electrodes.

Referring now to FIG. 3, a perspective view of an example of an adjustable EEG headset 300 with attached electrodes is depicted. In this example, the headset 300 includes the components discussed above (and shown in FIGS. 1A-1C). The headset 300 also includes a set of electrodes that are used to collect EEG measurements. Because the electrodes are attached into the headset 300, force loading on the sensors can be more easily accomplished for collecting precise and accurate EEG measurements. The headset 300 is also easier to be placed on a user compared to other headsets that have separate electrode placement mechanisms since electrode wires are run through the straps of the headset, which thereby prevents many complications relating to headset placement prior to EEG imaging.

In the example depicted in FIG. 3, the headset 300 includes three electrodes 302, 304, and 306 that are attached into the front portion 102A of the strap 102A (as discussed above in reference to FIGS. 1A-1F). The sensors 302, 304, and 306 can be attached into the front portion 102A using any suitable attachment means, such as stitching, adhesive-based attachment, hook and fastener-attachment, among others, that ensures that the sensors are contact with the forehead of the user's head. In other implementations, greater or less than three electrodes can also be attached into the front portion 102A of the strap 102.

The headset 300 includes additional sensors 308, 310, 312, and 314 that are hung off the straps to allow placement on different areas of the user's head. For example, the electrode 312 can be placed near the right of the user's nose above the cheek, the electrode 310 can be placed near the chin of the user's head, and the electrode 314 can be placed near the temple of the user's head. Other suitable electrode placement techniques are also contemplated.

Electrical wires 120 associated with the electrodes are affixed to the straps and run along to the headset to prevent interference with headset placement on the user's head. For example, as shown in FIG. 3, the wires 320 are initially run along the front portion 102A of the strap 102, continue along the side portion 102B of the strap 102, and then along the top of the headset above the strap 106. Individual wires associated with the hanging electrodes 308, 310, 312, and 314 can be bundled with the electrical wires 320 at specified locations to improve wire management. The electrical wires 120 can connect to an external cable (not shown in FIG. 3) that is then connected to a computing device that used to collect EEG measurements.

The figures discussed above are intended to depict examples of headsets with elastic and inelastic straps placed in specified parts of the headset, although other possible configurations are also contemplated within this specification. In some implementations, the elastic and inelastic straps of the headset can are arranged relative to another to improve the consistency of sensor placement with respect to a specific disease condition. For example, if the frontal lobe is of particular interest for a disease, then the region of the headset that is to be disposed on an area of the user's head corresponding to the user's head can incorporate a greater number of non-elastic straps to hold sensors, and the areas of non-interest (e.g., back lobe) can incorporate a greater number of elastic straps to provide support and self-adjusting force loading. As another example, in some instances, the left side of the headset can have sensors placed in inelastic straps, and the right side can have straps that are adjustable to improve adjustment. In this respect, different implementations can focus on a given area (or areas) of the user's head (e.g., left temple and base of spinal column) that are desired for a particular area of interest.

This specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

A number of embodiments have been described. Nevertheless, it will be understood that various modifications can be made without departing from the spirit and scope of the invention. In addition, the logic flows depicted in the figures do not require the particular order shown, or sequential order, to achieve desirable results. In addition, other steps can be provided, or steps can be eliminated, from the described flows, and other components can be added to, or removed from, the described systems. Accordingly, other embodiments are within the scope of the following claims.

The invention claimed is:

1. An electroencephalography (EEG) headset comprising:
a web comprising:
a plurality of inelastic straps extending between a first attachment and a second attachment, and
at least one electroencephalogram (EEG) electrode coupled to each inelastic strap,
wherein the web is arranged to span a portion of a crown of a user's head when worn by the user;
a first elastic strap coupled to the first attachment;
a front inelastic strap connected to the first elastic strap;
a second elastic strap coupled to the second attachment;
a back inelastic strap connected to the second elastic strap;
a chin strap; and
a third elastic strap arranged to connect the front and back inelastic straps to the chin strap, wherein the third elastic strap is connected to one of the front or back inelastic straps and, when worn, weaves through a first connector of the other of the front or back inelastic straps and through a second connector of the chin strap such that tension applied to the chin strap draws the front and the back inelastic straps together.

2. The headset of claim 1, comprising a plurality of connectors, wherein the plurality of connectors comprises:
a first set of connectors that couples the second elastic strap to the back inelastic strap;
a second set of connectors that couples the first elastic strap to the front inelastic strap.

3. The headset of claim 1, wherein the at least one EEG electrode comprises:
three EEG electrodes that are coupled to each inelastic strap and configured to contact a top of the user's head when worn by the user.

4. The headset of claim 1, wherein the first attachment is stitched to a portion of the first elastic strap, and the second attachment is stitched to a portion of the second elastic strap.

5. The headset of claim 1, wherein:
the at least one EEG electrode is configured to contact a user's head when the headset is worn by a user; and
the headset further comprises a plurality of wires for the at least one EEG electrode and configured to connect to at least one of the first elastic strap, the front inelastic strap, the second elastic strap, or the back inelastic strap.

6. The headset of claim 1, wherein an arrangement of the first elastic strap, second elastic strap, and third elastic strap is configured to evenly distribute pressure among the at least one EEG electrode.

7. An electroencephalography (EEG) headset comprising:
a central pressure distribution strap comprising
a topside inelastic portion having a first end connected to a first y-shaped elastic strap and a second end connected to a second y-shaped elastic strap;

a front inelastic strap comprising a first end connected to a first leg of the first y-shaped elastic strap and a second end connected to a second leg of the first y-shaped elastic strap;
a back inelastic strap comprising a first end connected to a first leg of the second y-shaped elastic strap and a second end connected to a second leg of the second y-shaped elastic strap; and
at least one EEG electrode coupled to the inelastic portion of the central pressure distribution strap,
wherein the central pressure distribution strap is sized such that, when worn by a user, the front inelastic strap extends over a forehead of the user and the back inelastic strap extends over a back portion of a head of the user;
a chin strap; and
a third elastic strap arranged to connect the front and back inelastic straps to the chin strap, wherein the third elastic strap is connected to one of the front or back inelastic straps and, when worn, weaves through a first connector of the other of the front or back inelastic straps and through a second connector of the chin strap such that tension applied to the chin strap draws the front and the back inelastic straps together.

8. The headset of claim 7, wherein the first end and second end of the topside inelastic portion of the central pressure distribution strap are stitched to the first y-shaped elastic strap and the second y-shaped elastic strap.

9. The headset of claim 8, wherein the at least one EEG electrode comprises:
three EEG electrodes that are coupled to the front inelastic strap of the central pressure distribution strap and configured to contact the forehead of the user when worn by the user; and
a fourth electrode that is coupled to the topside inelastic portion of the central pressure distribution strap and configured to contact a top of the head of the user when worn by the user.

10. The headset of claim 7, wherein:
the at least one EEG electrode is configured to contact the user's head when the headset is worn by the user; and
the headset further comprises a plurality of wires for the at least one EEG electrode and configured to connect to the central pressure distribution strap.

11. An electroencephalography (EEG) headset comprising:
a central strap configured to be placed over a crown of a head when worn, the central strap comprising front and back inelastic portions joined by at least one elastic portion;
at least one EEG electrode coupled to the central strap;
a chin strap; and
an elastic strap arranged to connect the front and back inelastic portions of the central strap to the chin strap, wherein the elastic strap is connected to one of the front or back inelastic portions of the central strap and, when worn, weaves through a first connector of the other of the front or back inelastic portions and through a second connector of the chin strap such that tension applied to the chin strap draws the front and the back inelastic portions together.

12. The headset of claim 11, wherein:
the central strap comprises a topside inelastic portion;
the at least one elastic portion of the central strap comprises:
a first elastic portion that joins the front inelastic portion to the topside inelastic portion, and
a second elastic portion that joins the back inelastic portion to the topside inelastic portion.

13. The headset of claim 12, wherein the at least one EEG electrode comprises:
three EEG electrodes that are coupled to the front inelastic portion of the central strap and configured to contact a forehead of a user's head when worn by a user; and
a fourth electrode that is coupled to the topside inelastic portion of the central strap and configured to contact the top of the user's head when worn by the user.

14. The headset of claim 12, wherein the topside inelastic portion of the central strap is stitched to a portion of the elastic strap.

15. The headset of claim 12, wherein the topside inelastic portion is stitched to the first elastic portion and second elastic portion.

16. The headset of claim 1, wherein at least one inelastic strap of the plurality of inelastic straps comprises at least one branch.

17. The headset of claim 7, wherein the elastic strap is connected to the one of the front or back inelastic portions of the central strap at a first end of the elastic strap and a first location on the one of the front or back inelastic portions of the central strap, and
wherein the elastic strap is further arranged, when worn, to pass over the head, through a third connector attached to the chin strap, through a fourth connector attached to the other of the front or back inelastic portion, and is connected to the one of the front or back inelastic portions of the central strap at a second location of the front or back inelastic portions of the central strap.

18. The headset of claim 7, wherein the elastic strap is connected to the one of the front or back inelastic portions of the central strap at a first end of the elastic strap and a first location on the one of the front or back inelastic portions of the central strap, and wherein the elastic strap is further arranged, when worn, to pass over the head, through a third connector attached to the chin strap, through a fourth connector attached to the other of the front or back inelastic portion, and is connected to the one of the front or back inelastic portions of the central strap at a second location of the front or back inelastic portions of the central strap.

19. The headset of claim 11, wherein the elastic strap is connected to the one of the front or back inelastic portions of the central strap at a first end of the elastic strap and a first location on the one of the front or back inelastic portions of the central strap, and wherein the elastic strap is further arranged, when worn, to pass over the head, through a third connector attached to the chin strap, through a fourth connector attached to the other of the front or back inelastic portion, and is connected to the one of the front or back inelastic portions of the central strap at a second location of the front or back inelastic portions of the central strap.

* * * * *